United States Patent
Aghanouri

(10) Patent No.: US 10,551,536 B2
(45) Date of Patent: Feb. 4, 2020

(54) INFRARED RADIATION TRANSPARENT SUBSTRATES AND SYSTEMS AND METHODS FOR CREATION AND USE THEREOF

(71) Applicant: THE NORTH FACE APPAREL CORP., Wilmington, DE (US)

(72) Inventor: Abolfazi Aghanouri, Richmond, CA (US)

(73) Assignee: THE NORTH FACE APPAREL CORP., Wilmington, DE (US)

(*) Notice: Subject to any disclaimer, the term of this patent is extended or adjusted under 35 U.S.C. 154(b) by 82 days.

(21) Appl. No.: 15/877,979

(22) Filed: Jan. 23, 2018

(65) Prior Publication Data

US 2018/0210123 A1 Jul. 26, 2018

Related U.S. Application Data

(60) Provisional application No. 62/450,959, filed on Jan. 26, 2017.

(51) Int. Cl.
*A41D 1/02* (2006.01)
*A41D 1/04* (2006.01)
(Continued)

(52) U.S. Cl.
CPC ............. *G02B 5/208* (2013.01); *A41B 1/00* (2013.01); *A41B 9/00* (2013.01); *A41C 3/005* (2013.01); *A41D 1/02* (2013.01); *A41D 1/04* (2013.01); *A41D 1/089* (2018.01); *A41D 1/14* (2013.01); *A41D 7/00* (2013.01); *A41D 17/02* (2013.01); *A41D 19/00* (2013.01); *A42B 1/00* (2013.01); *A43B 1/0072* (2013.01); *D02G 3/44* (2013.01); *A41D 2500/20* (2013.01);
(Continued)

(58) Field of Classification Search
CPC .......... B02B 5/208; A41D 1/089; A41D 1/02; A41D 1/04; A41D 1/14; A41D 7/00; A41D 17/02; A41D 19/00; A41B 1/00; A41B 9/00; A41C 3/005; A42B 1/00; A43B 1/0072
USPC .......................................................... 526/351
See application file for complete search history.

(56) References Cited

U.S. PATENT DOCUMENTS 7,622,188 B2 * 11/2009 Kamiyama .............. D01D 5/36
385/131

FOREIGN PATENT DOCUMENTS

JP   S63165579   7/1988
JP   H10251953   9/1998
(Continued)

OTHER PUBLICATIONS

PCT International Search Report and Written Opinion in PCT/US2018/015281, dated Jun. 12, 2018, 27 pages.

*Primary Examiner* — William K Cheung
(74) *Attorney, Agent, or Firm* — Smith, Gambrell & Russell, LLP

(57) ABSTRACT

Substrates with transparency to infrared body radiation and opacity in the visible light spectrum are provided and systems and methods for creation thereof are provided. The IR radiation transparent substrate is IR radiation transparent and visible light opaque with enough breathability and softness to make it suitable for use in garments for body thermal regulation. Further, the IR radiation transparent substrate is created utilizing nanofiber technology to form specific sized micro pores between the nanofibers.

20 Claims, 7 Drawing Sheets

(51) Int. Cl.
  *A41D 1/089*   (2018.01)
  *A41D 1/14*   (2006.01)
  *A41B 9/00*   (2006.01)
  *A41D 7/00*   (2006.01)
  *A41D 17/02*   (2006.01)
  *A41D 19/00*   (2006.01)
  *A42B 1/00*   (2006.01)
  *D02G 3/44*   (2006.01)
  *A41B 1/00*   (2006.01)
  *G02B 5/20*   (2006.01)
  *A41C 3/00*   (2006.01)
  *A43B 1/00*   (2006.01)

(52) U.S. Cl.
  CPC .... *A41D 2500/30* (2013.01); *D10B 2321/021* (2013.01); *D10B 2321/022* (2013.01); *D10B 2401/04* (2013.01); *D10B 2401/10* (2013.01); *D10B 2401/20* (2013.01); *D10B 2501/00* (2013.01)

(56) References Cited

FOREIGN PATENT DOCUMENTS

JP    2011132631    7/2011
WO    2016044609    3/2016

\* cited by examiner

INFRARED RADIATION TRANSPARENT SUBSTRATES AND SYSTEMS AND METHODS FOR CREATION AND USE THEREOF

INTRODUCTION

Clothing and fabric manufacturers are always looking for ways to improve their materials and/or garments. For example, manufacturers may try to select materials with specific properties to create a garment for specific purposes, such as athletic apparel, swimwear, ski gear, etc.

It is with respect to these and other general considerations that aspects disclosed herein have been made. Also, although relatively specific problems may be discussed, it should be understood that the aspects should not be limited to solving the specific problems identified in the background or elsewhere in this disclosure.

SUMMARY

In summary, the disclosure generally relates to a substrate that is transparent to infrared (IR) body radiation and visible light opaque and systems and methods for creation and use thereof.

One aspect of the disclosure is directed to a method for creating an infrared radiation transparent and visible light opaque substrate. The method includes:
  selecting an infrared radiation transparent and visible light transparent polymer;
  creating nanofibers out of the polymer, wherein micro pores are formed between the nanofibers,
  the micro pores scatter visible light to change the polymer from being visible light transparent to being visible light opaque;
  the micro pores are large enough to be air permeable; and
  forming an infrared radiation transparent and visible light opaque fabric from the nanofibers.

In another aspect, the disclosure is directed to an infrared (IR) radiation transparent and visibly opaque substrate. The infrared (IR) radiation transparent and visibly opaque substrate includes nanofibers of an IR radiation transparent polymer and pores between the nanofibers large enough to scatter visible light and for air permeability. The nanofibers have a diameter from 50 nm to 1000 nm. The pores have a size from 400 nm to 1500 nm.

In yet another aspect of the disclosure, the disclosure is directed to a method for creating an infrared radiation transparent and visible light opaque garment. The method includes:
  selecting an infrared radiation transparent and visible light transparent polymer;
  creating island-of-the-sea microfibers from the polymer;
  creating a visible light transparent garment utilizing the microfibers; and
  applying a solvent to the garment that dissolves a sea component in the microfibers to form nanofibers of the polymer and to form pores between the nanofibers.
The pores are sized from 400 nm to 1500 nm and change the garment from visible light transparent to visible light opaque.

This summary is provided to introduce a selection of concepts in a simplified form that are further described below in the Detailed Description. This summary is not intended to identify key features or essential features of the claimed subject matter, nor is it intended as an aid in determining the scope of the claimed subject matter.

These and other features and advantages will be apparent from a reading of the following detailed description and a review of the associated drawings. It is to be understood that both the foregoing general description and the following detailed description are illustrative only and are not restrictive of the claims.

BRIEF DESCRIPTION OF THE DRAWINGS

Non-limiting and non-exhaustive examples or aspects are described with reference to the following Figures.

DETAILED DESCRIPTION

Figure 1:
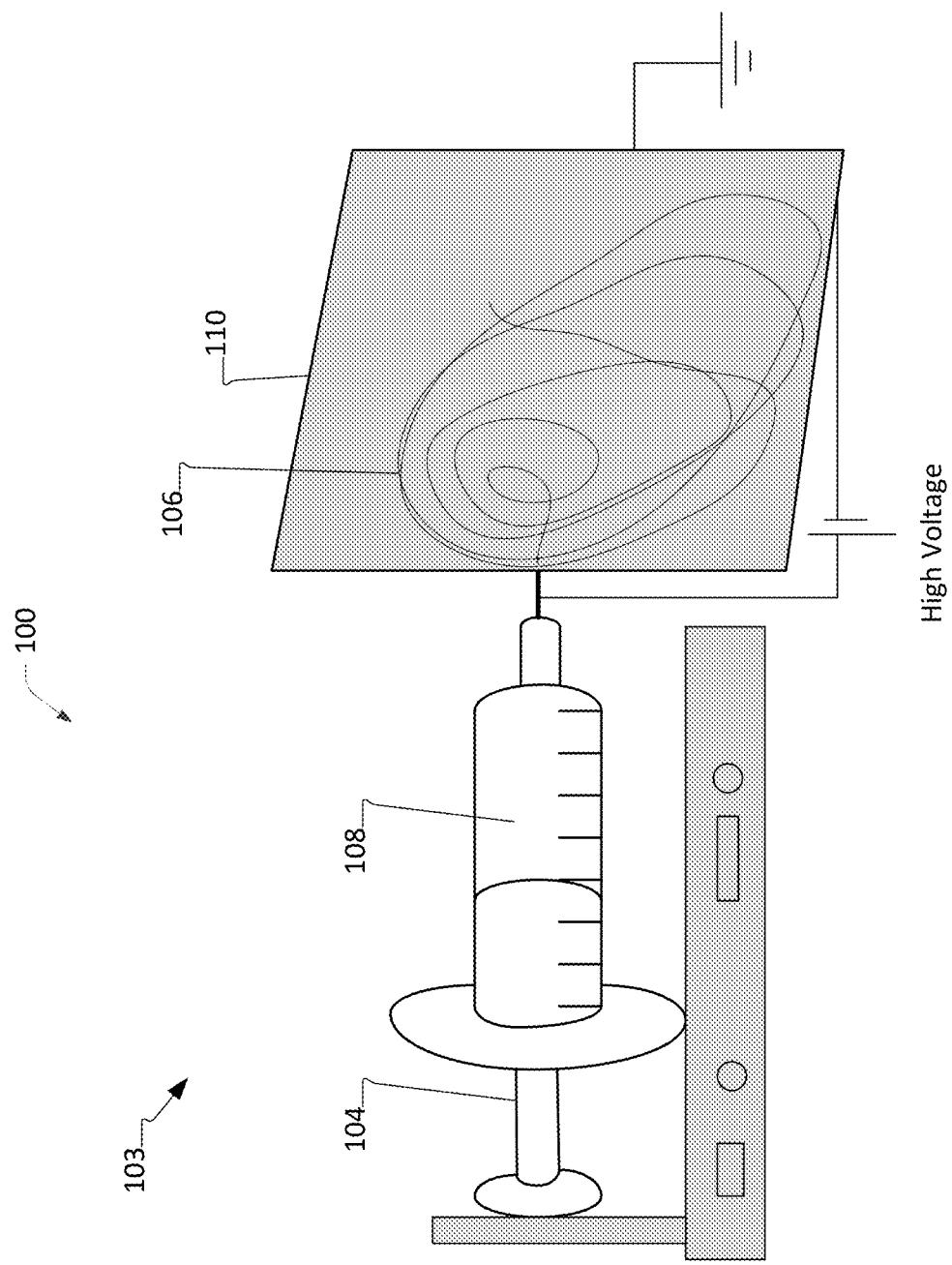
FIG. 1 is a schematic diagram illustrating a nanofiber creation system, in accordance with aspects of the disclosure.

In the following detailed description, references are made to the accompanying drawings that form a part hereof, and in which are shown by way of illustrations specific embodiments, aspects, or examples. These aspects or examples may be combined, other examples may be utilized, and structural changes may be made without departing from the spirit or scope of the disclosure. The following detailed description is therefore not to be taken in a limiting sense.

More than 60% of upper body heat can be lost through infrared (IR) radiation. However, most textile-based polymers are not transparent to this type of IR radiation (>700 nm). Accordingly, most clothes trap heat generated by the body and have low heat transfer rates. Polymers with high transparency in this IR spectrum are desired to achieve higher heat transfer rates and better thermal regulation for clothing. However, polymers which are transparent to this type of IR radiation are transparent in the visible light region, so visible light flows freely through textiles that are transparent in this IR radiation range. Substrates need to be opaque in the visible range to be qualified for apparel applications. Additionally, IR radiation transparent textiles are often hard and not breathable. As such, these IR radiation transparent textiles are not suitable for clothing or garments.

A recent study discovered that polyethylene (PE) films (an IR-transparent polymer) could be stretched to form a film with micro pores of 400-700 nm diameters. The created micro pores scattered visible light making the PE film opaque. However, because of the mechanical properties of the stretched PE film, such as being thin, hard, and not breathable, this stretched material is not conducive for garment production.

There are typically no materials that are inherently transparent in the body IR radiation range, opaque in the visible light spectrum range, breathable, and soft enough for garment production. Further, there are no systems or methods for creating these types of materials.

Therefore, the systems and methods disclosed herein provide an IR radiation transparent and visible light opaque substrate and also provide systems and methods for creation and/or use thereof. The substrate of the systems and method disclosed herein is a breathable, soft, IR body radiation transparent, and visible light opaque. The substrate is formed by creating nanofibers out of an IR radiation transparent material, such as a polymer. The fineness and thinness of the nanofibers is controlled to increase the softness and tenacity of the substrate. Additionally, the nanofibers are configured or formed with pores from 400 nm to 1500 nm between the nanofibers. These pores scatter light creating the opacity needed for garment production. Further, these pores are large enough to be air permeable making the fabric breathable. As such, the IR radiation transparent and opaque substrate may be utilized in garments to form garments with high IR radiation transfer rates to allow body heat to transfer easily out of the garments.

A substrate as utilized herein refers to a fabric or a garment created from a fabric. A fabric as utilized herein refers to any woven, nonwoven, or compound material that is suitable for garment production. A woven fabric as utilized herein refers to any material that has been created from weaving or knitting. A nonwoven fabric as utilized herein refers to any sheet or web structure that has been created from mechanically, thermally, and/or chemically entangling fibers or filaments.

Referring now to the drawings, in which like numerals represent like elements through the several figures, various aspects of the present disclosure will be described. FIGS. 1-4 are schematic diagrams illustrating different nanofiber creation systems 100 for creating nanofibers 106 from an IR radiation transparent and visible light transparent polymers 108, in accordance with an aspect of the disclosure. The nanofibers 106 are fabricated to create an IR radiation transparent and visibly opaque fabric 102, as illustrated in FIG. 2.

Figure 2:
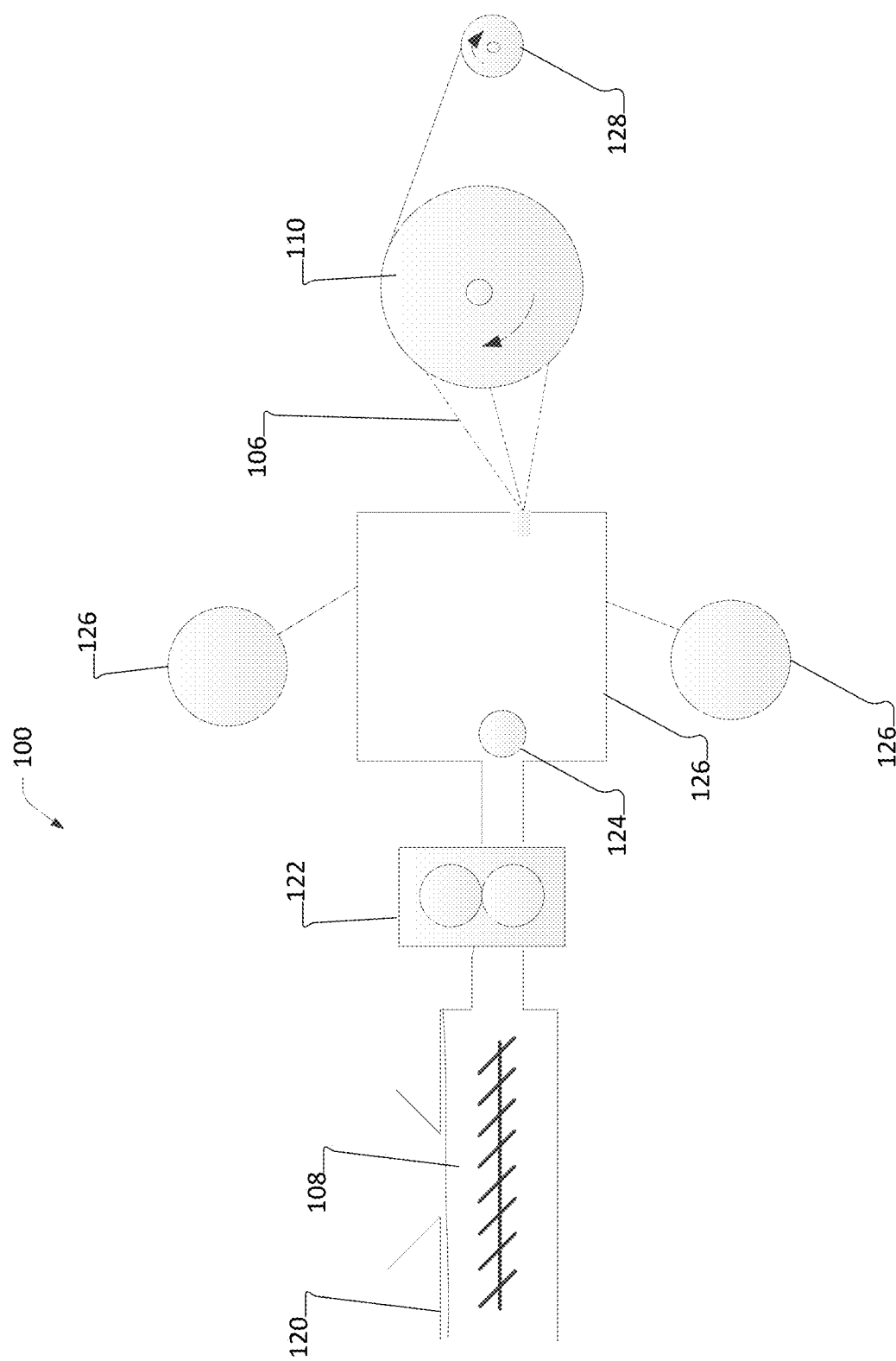
FIG. 2 is a schematic diagram illustrating a nanofiber creation system, in accordance with aspects of the disclosure.

FIG. 1 illustrates a melt electrospinning nanofiber creation system 103. In FIG. 1, an IR radiation transparent polymer solution 108 is extruded through an electrified spinneret 104 to create a nanofiber 106, which is gathered on a collector 110. Further, micro pores are formed between the IR radiation transparent polymer nanofibers 106 during formation and/or fabrication of the nanofibers 106. The micro pores between the nanofibers 106 change the polymer from visible light transparent to visible light opaque because the pores are sized to scatter light.

FIG. 2 illustrates a melt blowing nanofiber creation system 112. In FIG. 2 a melted solution of the IR radiation transparent polymer 108 is extruded through an extruder 120. Next, the extruded IR radiation transparent polymer is sent through a gear pump 122 and then through a die 124 in an air manifold 126 that sprays a nanofiber 106 onto a rotating collector 110. The formed nanofibers 106 are gathered onto a winder 128, which is also rotating. Further, micro pores are formed between the IR radiation transparent polymer nanofibers 106 during formation and/or fabrication of the nanofibers 106. The micro pores between the nanofibers 106 change the polymer from visible light transparent to visible light opaque because the pores are sized to scatter light.

Figure 3:
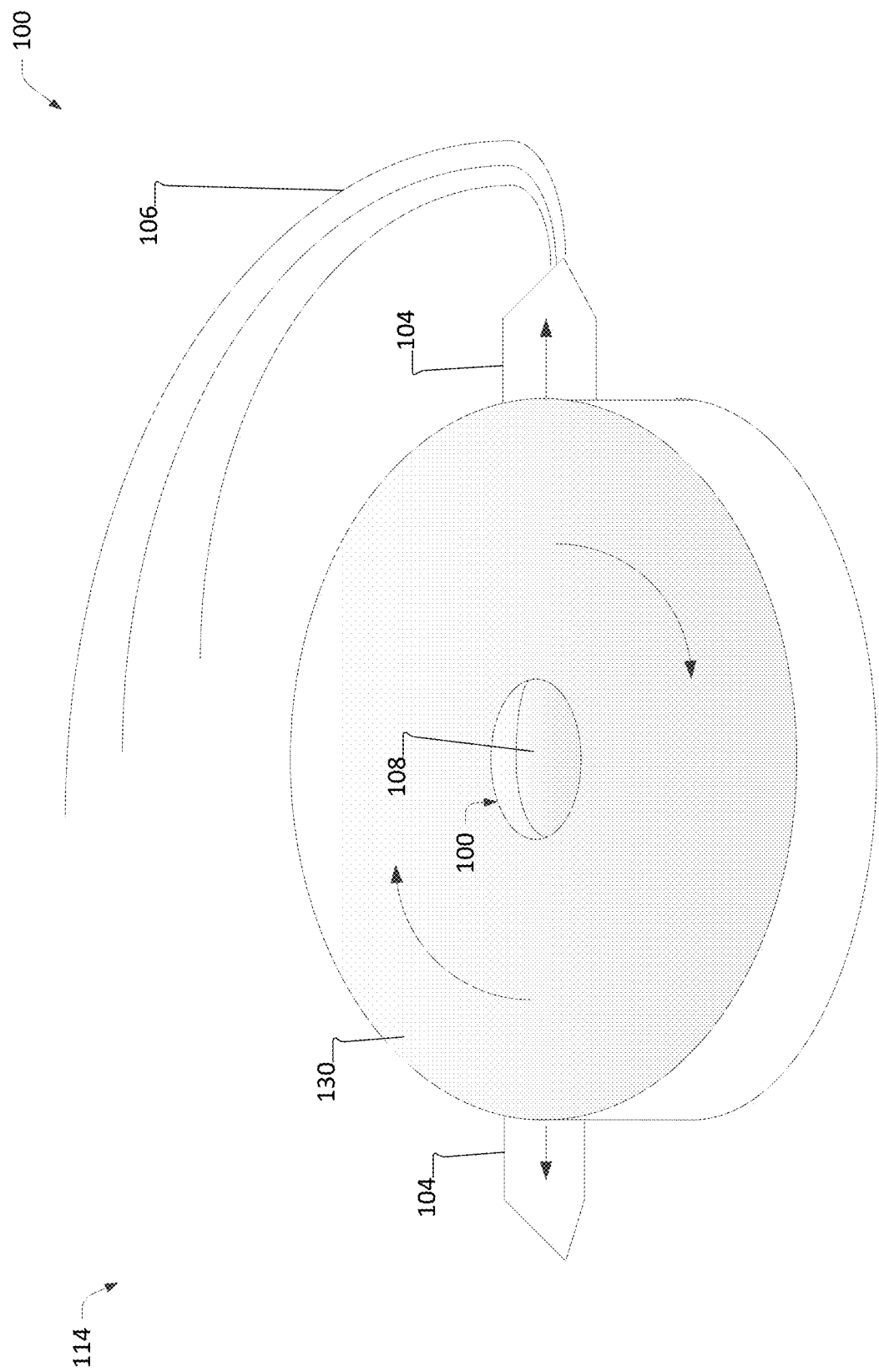
FIG. 3 is a schematic diagram illustrating a nanofiber creation system, in accordance with aspects of the disclosure.

FIG. 3 illustrates a force spinning nanofiber creation system 114. The IR radiation transparent polymer solution 108 is inserted into the centrifugal spinner 130. The centrifugal spinner 130 rotates or spins and extrudes the IP transparent polymer solution 108 through the spinnerets 104 to form nanofibers 106. Further, micro pores are formed between the IR radiation transparent polymer nanofibers 106 during formation and/or fabrication of the nanofibers 106. The micro pores between the nanofibers 106 change the polymer from visible light transparent to visible light opaque because the pores are sized to scatter light.

Figure 4:
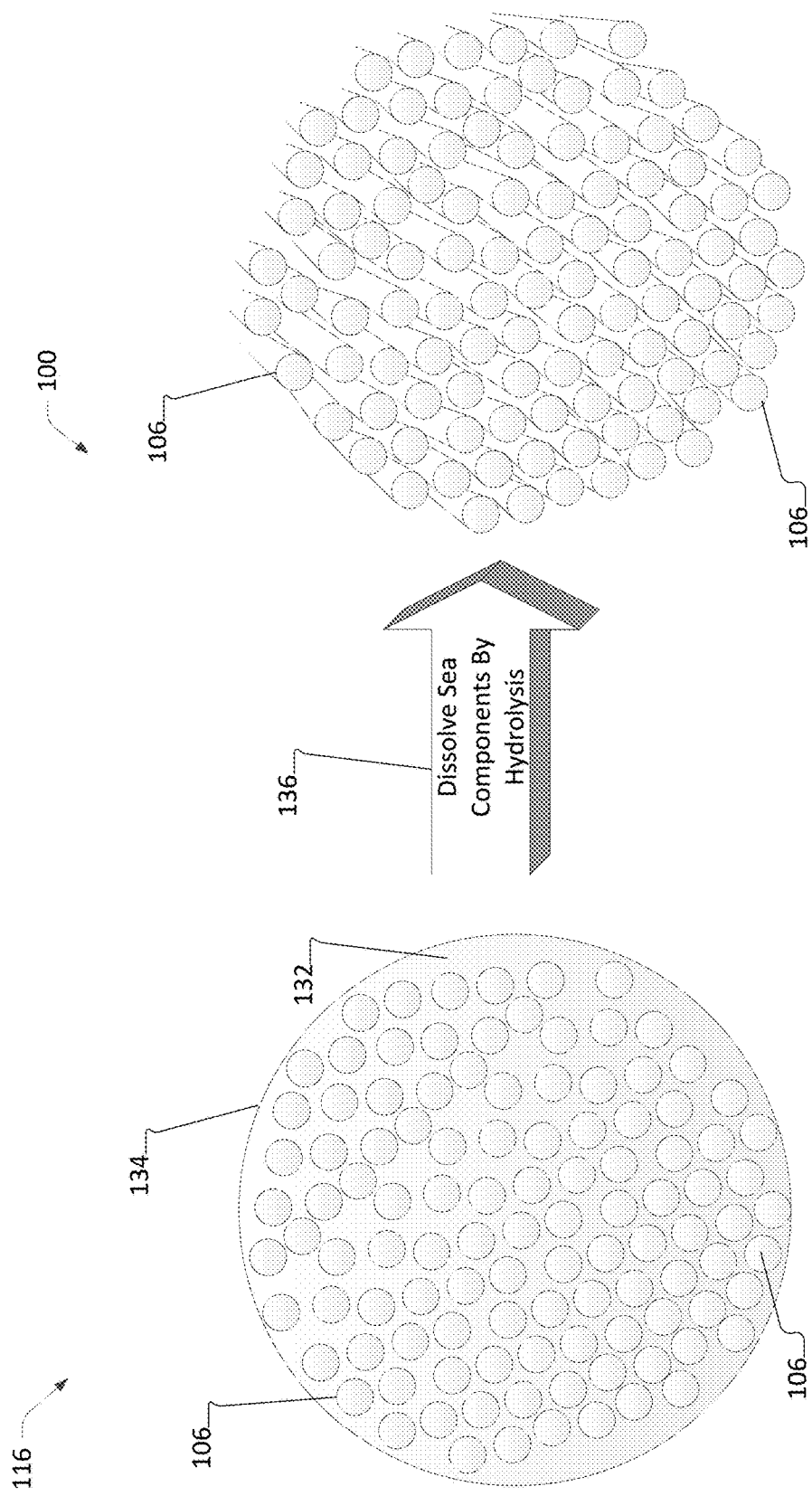
FIG. 4 is a schematic diagram illustrating a portion of a nanofiber creation system, in accordance with aspects of the disclosure.
Figure 5:
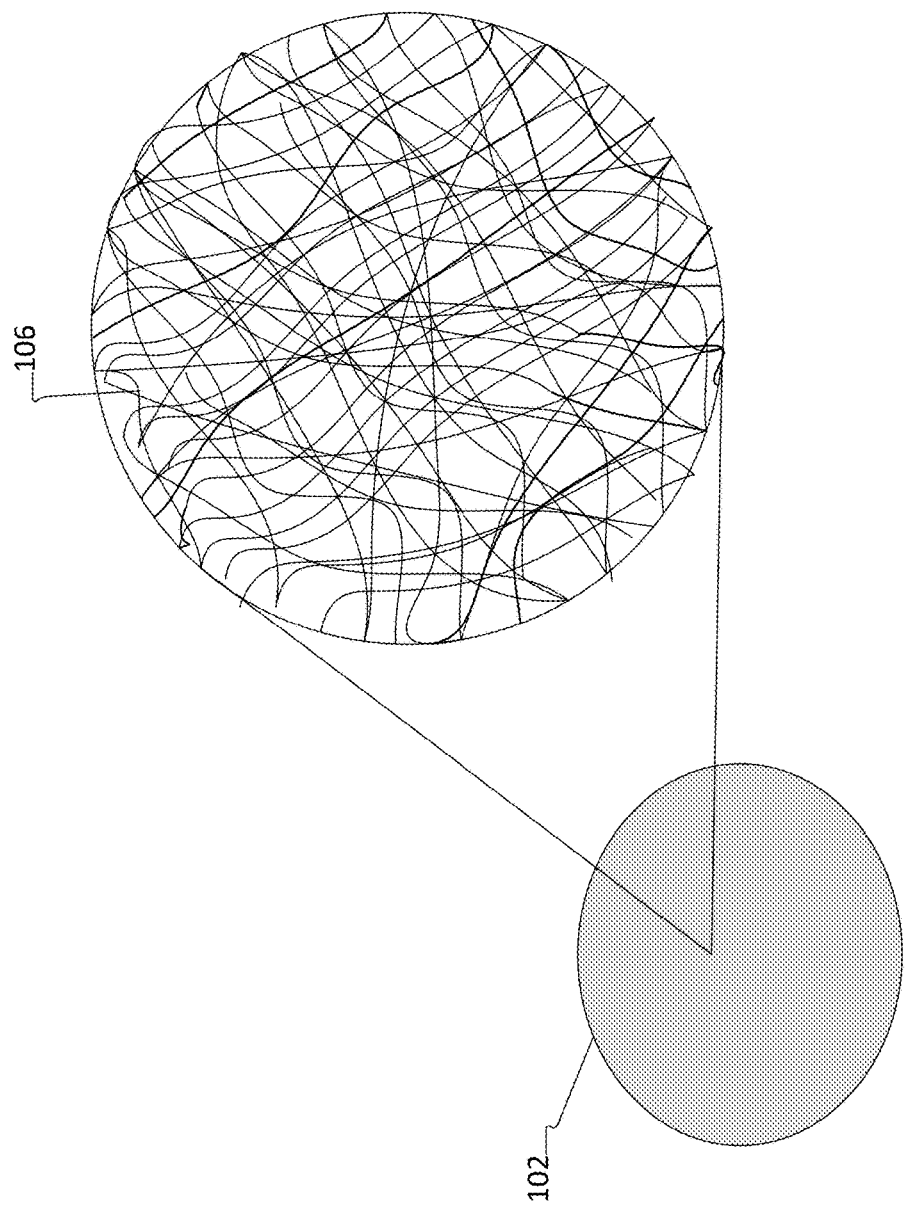
FIG. 5 is schematic diagram illustrating an IR radiation transparent substrate and a magnified view of the nanofibers of the substrate, in accordance with aspects of the disclosure.

FIG. 4 illustrates a portion of an island-in-the-sea extrusion nanofiber creation system 116. FIG. 4 illustrates a cross-section of an island-in-the-sea microfiber 134, created from the island-in-the-sea extrusion of IR polymer chips 108 and a sea component 132. FIG. 4 illustrates the IR transparent polymer nanofibers 106 held together by the sea component 132 in the island-in-the-sea microfiber 134. The island-in-the-sea microfiber 134 is washed in solvent to dissolve the sea component through hydrolysis 136 to form aligned nanofibers 106 of the IR radiation transparent polymer. Further, micro pores are formed between the aligned IR radiation transparent polymer nanofibers 106 during formation of the nanofibers 106. Because the nanofibers 106 are aligned at formation they create a yarn-like material. The micro pores between the nanofibers 106 change the polymer from visible light transparent to visible light opaque because the pores are sized to scatter light.

This list is not mean to be limiting. Any suitable nanofiber creation system 100 may be utilized to create the nanofibers from the IR radiation transparent and visible light transparent polymers. For example, other suitable creation systems 100 include melt electrospinning, centrifugal melt electrospinning, and hot air assisted melt electrospinning.

The IR radiation transparent and visible light transparent polymers are hydrocarbon polymers. Examples of the IR radiation transparent and visible light transparent hydrocarbon polymers include PE or polypropylene (PP). This list is not meant to be limiting. Any suitable IR radiation transparent and visible light transparent hydrocarbon polymers may be utilized in the creation system 100.

The creation systems 100 in FIGS. 1-3 include a spinneret 104 that creates nanofibers 106 from a solution of the IR radiation transparent and visible light transparent polymer 108. The structure of the nanofibers may be specifically configured using specific temperatures, application speed, and an extruding die on the spinneret 104. For example, very fine nanofibers structures may be created using one or more of these techniques. The fine fibers may increase the softness and improve the mechanical properties, such as tenacity, of the IR radiation transparent material when compared to stretched IR radiation transparent polymers that are also opaque. During electrospinning as showing in FIG. 1, high voltage and specific temperatures may be utilized to spay the nanofibers onto a collector 110. The spinneret 104 may utilize melt electrospinning, force-spinning, centrifugal melt electrospinning, hot air assisted melt electrospinning, hot air assisted melt blown and/or spun bond to spin nanofiber materials from IR radiation transparent and visible light transparent polymers 108.

The spinneret 104 may be spun to create nanofiber materials to make nonwoven, multifilament yarns, woven, knit and/or compound material construction for IR radiation transparent garments. FIG. 2 illustrates an IR radiation transparent fabric 102 and a zoomed in view of the nanofibers in nonwoven/compound forms 106 of the fabric 102, in accordance with aspects of the disclosure.

As illustrated in FIG. 4, an island-in-the-sea extrusion technique can be used to make nanofibers from an IR radiation transparent and visible light transparent polymer 108. In this technique, an island-in-the-sea microfiber 134 is extruded from the IR radiation transparent and visible light transparent polymer 108 and a sea component. The microfiber 134 may be sized from 1 micron to 5 microns and contains several nanofibers 106 held together by the sea component 132. The nanofibers 106 within the island-in-the-sea microfiber 134 may be sized from 50 nm to 1000 nm.

In some aspects, the island-in-the-sea microfibers 134 are fabricated to make woven, knitted, nonwoven and/or compound fabrics. The fabric created from the island-in-the-sea microfibers 134 may be utilized to make garments. In these aspects, once the garment is formed from the island-in-the-sea microfiber fabric, the garment is washed with an appropriate solvent to dissolve the sea 132 component with hydrolysis. In some aspects, the sea component 132 in the island-in-the-sea microfiber 134 is polyvinyl alcohol. However, any suitable sea component may be utilized to create the island-in-the-sea microfibers.

Alternatively, the fabric created from the island-in-the-sea microfiber 134 may be treated with an appropriate solvent to dissolve the sea component with hydrolysis 136 prior to being made into a garment. In these aspects, the fabric prior to being cut and sewn into a garment is made of nanofibers 106 instead of the island-in-the-sea microfibers 134. The nanofiber fabric may then be cut and sewn into a garment.

In other aspects, the island-in-the-sea microfibers 134 may be washed with the appropriate solvent to dissolve the sea component with hydrolysis 136 prior to being made into a fabric. As illustrated in FIG. 4, the nanofibers 106 created by dissolving the sea are aligned and run in the same direction. As such, the nanofibers 106 are formed in a yarn-like configuration. In these aspects, the yarn like nanofibers 106 are fabricated to form woven, knitted, nonwoven and/or compound fabrics with transparency to IR regions and opacity to the visible light spectrum range. The nanofiber fabric may then be cut and sewn into a garment.

The nanofibers created from any of the listed techniques can be fabricated to form woven, knitted, nonwoven and/or compound fabrics with transparency to IR regions and opacity to the visible light spectrum range. The type of fabric created depends on the selected nanofiber creation system 100 and the fabrication technique. In some aspects, the fabrication techniques are the same techniques utilized to form conventional clothing materials such as fiber, yarn, thread, and fabric. In other aspects, the fabrication techniques have to be slightly altered for use with the created nanofibers to form the woven, knitted, nonwoven and/or compound fabrics with transparency to IR regions and opacity to the visible light spectrum range. For example, yarn drawing ratio, heat finishing, chemical finishing conditions and dyeing and printing formulations may have to be modified.

The IR radiation transparent fabrics are breathable due to the large pore sizes between the nanofibers created or engineered by the creation systems 100. Further, the fabricated IR radiation transparent substrate 102 is breathable without having to add any type of undesirable additives. In some aspects, the micro pore size between the nanofibers can be controlled to the 400-700 nm size to provide opacity and breathability. In other aspects, the pore size between the nanofibers is controlled to 500-1000 nm size to provide opacity and breathability. In other aspects, the pore size between the nanofibers is controlled to 800-1500 nm size to provide opacity and breathability. In other aspects, the pore size between the nanofibers is controlled to 1000-3000 nm size to provide opacity and breathability.

Additionally, the mechanical properties of the IR radiation transparent fabrics 102 are soft enough, thick enough and strong enough for garment construction. The IR radiation transparent fabrics 102 are softer and thicker than the stretched IR radiation transparent materials. In some aspects, the IR radiation transparent fabric 102 is softer because of a selected specific nanofibers structure, such as fine and thin nanofibers. The IR radiation transparent fabric 102 allows body heat in the IR spectrum to escape easily from the material. Further, the IR radiation transparent fabric 102 may also provide some wicking. As such, the IR radiation transparent fabric 102 is perfect for use in clothing, athletic gear, sleepwear, and/or other indoor/outdoor gear or any other garments where efficient body heat release is desirable.

Figure 6:
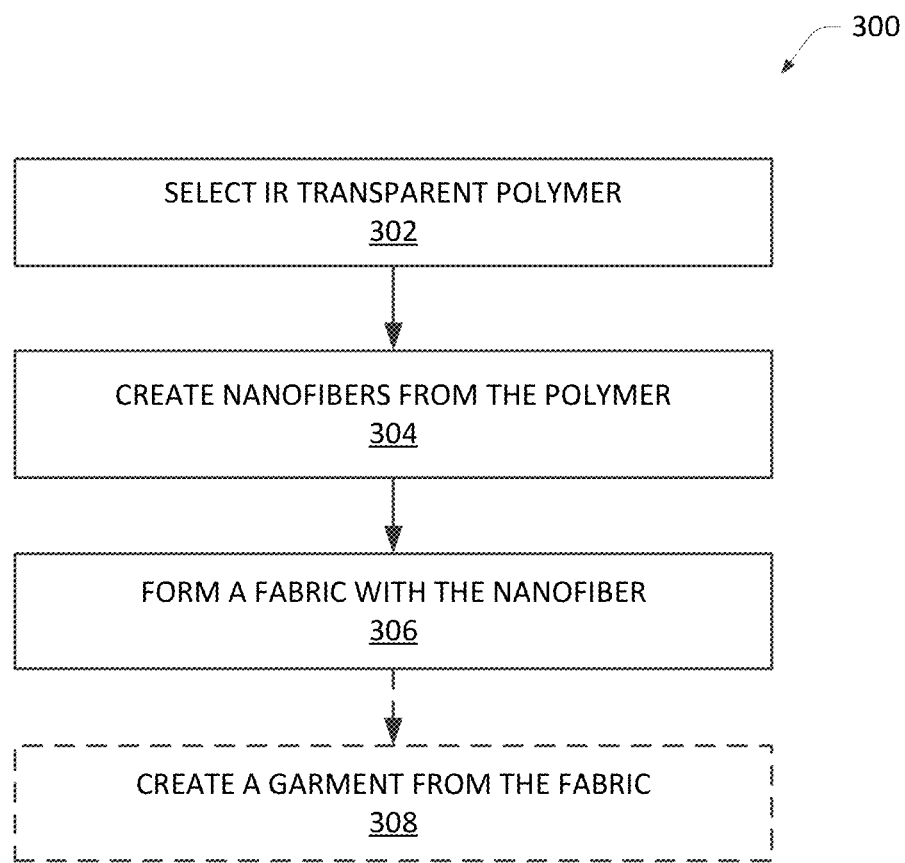
FIG. 6 is a flow diagram illustrating a method for creating an IR radiation transparent fabric, in accordance with aspects of the disclosure.

FIG. 6 is a flow diagram illustrating a method 300 for creating an IR radiation transparent and visibly opaque fabric. In some aspects, method 300 may be performed by systems 100 disclosed above.

Method 300 begins at operation 302, where an infrared radiation transparent polymer is selected. For example, the infrared radiation transparent polymer is a hydrocarbon polymer. The hydrocarbon polymers may be thermoset or thermoplastic. In some aspects, the IR radiation transparent polymer is PP or PE.

Next, at operation 304, nanofibers of the infrared radiation transparent polymer are created and collected. The nanofibers may be specifically structured to provide desired properties. In some aspects, the nanofibers are structure to be very fine fibers. In some aspects, the structure of the nanofibers may be affected by changing temperatures, voltage, application speeds, air speed, drawing ratio, and/or an extrusion die of the creation system. For example, the nanofibers may have a diameter from 50 nm to 1000 nm. In other aspects, the nanofibers may have diameter from 50 nm to 700 nm.

Further, the spaces formed between nanofibers may be controlled to create specifically sized micro pores that scatter visible light and are large enough to be air permeable either on the collector or in the final woven, knitted or compound fabric depending on the creation system. In some aspects, the extrusion is performed utilizing spun nanofiber technology, such as force spinning, electrospinning, melt electrospinning, electrical field assisted force spinning, hot air assisted melt electrospinning, melt blown or island-in-the-sea extrusion technology. In some aspects, the micro pores are from 400 nm to 700 nm in diameter. In other aspects, the micro pores are from 800 nm to 1500 nm in diameter.

At operation 306, the created nanofibers are gathered and fabricated to form an IR radiation transparent and visibly opaque fabric. The IR radiation transparent and visibly opaque fabric may be woven, knitted, nonwoven and/or compound fabrics. The type of fabric created depends on the selected nanofiber creation technology and the fabrication technique. In some aspects, the fabrication techniques are the same techniques utilized to form conventional clothing materials. In other aspects, the fabrication techniques have to be slightly altered for use with the created nanofibers to form the woven, knitted, nonwoven and/or compound fabrics with transparency to IR regions and opacity to the visible light spectrum range.

Is some aspects, method 300 includes operation 308. At operation 308, a garment is created from the IR radiation transparent and visibly opaque fabric. The garment may be created from cutting, sewing, knitting, weaving, and/or any other suitable garment creating techniques. A garment may be clothing, outerwear, outdoor gear, and/or any other suitable application for IR radiation transparent fabric. More specifically, the garment may be a pair of pants, a shirt, a skirt, a jacket, a pair of shorts, a vest, a hat, a pair of gloves, a dress, a pair of leggings, a pair of capris, a bra, a piece of underwear, a piece of swim wear, a pair of shoes, etc. This list is exemplary only and is not meant to be limiting. Any item of clothing or outerwear that may be worn by a person or animal may be a garment as utilized herein.

Figure 7:
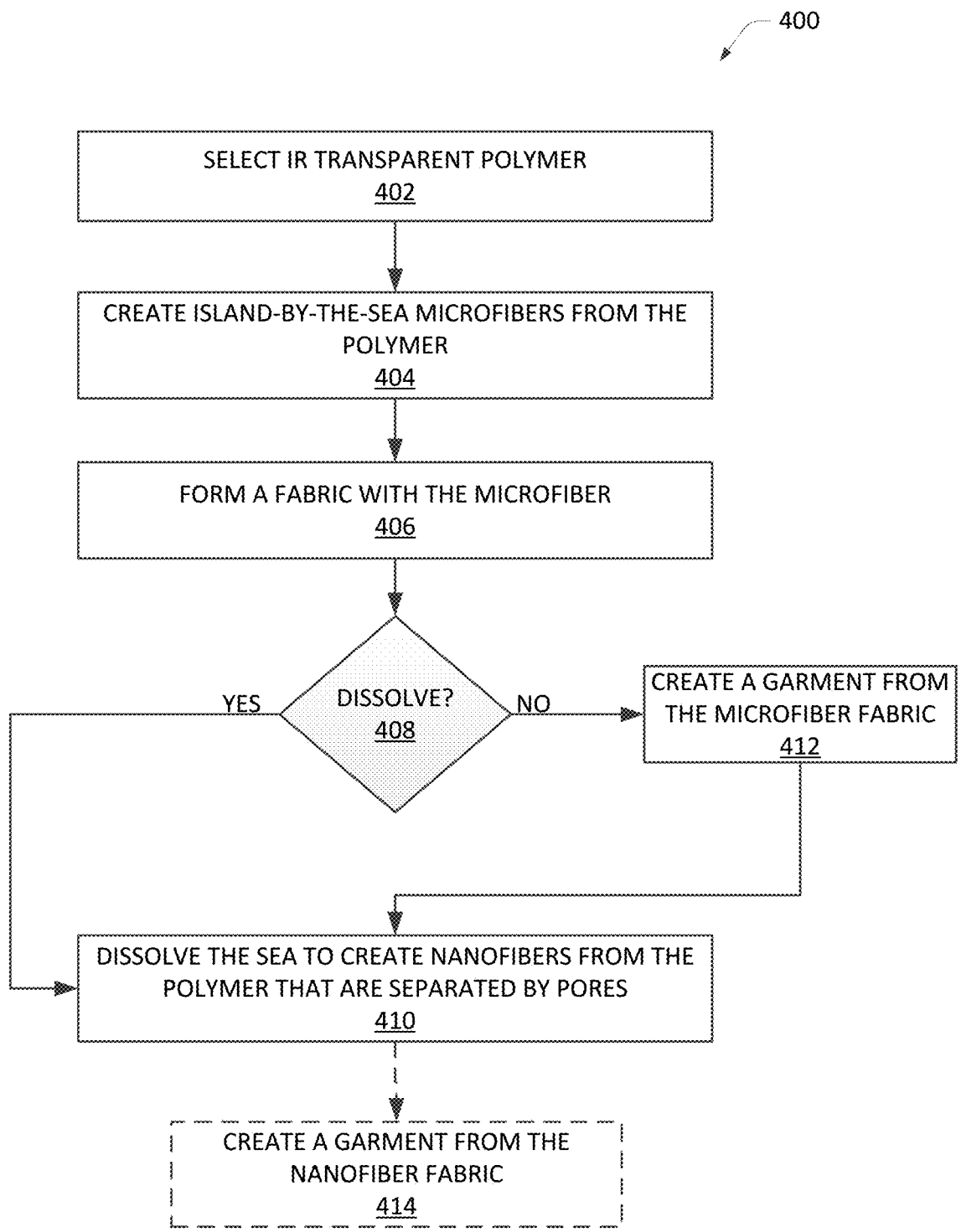
FIG. 7 is a flow diagram illustrating a method for creating an IR radiation transparent fabric, in accordance with aspects of the disclosure.

FIG. 7 is a flow diagram illustrating a method 400 for creating an IR radiation transparent and visibly opaque fabric. In some aspects, method 400 may be performed by island-in-the-sea system 100 disclosed above.

Method 400 begins at operation 402 where an infrared radiation transparent polymer is selected. For example, the infrared radiation transparent polymer is a hydrocarbon polymer. The hydrocarbon polymers may be thermalset or thermoplastic. In some aspects, the IR radiation transparent polymer is PP or PE.

Next, at operation 404, island-of-the-sea microfibers are created from the IR radiation transparent polymer and a sea component. The island-of-the-sea microfibers are created by utilizing an island-of-the-sea extrusion process. The microfibers may be specifically structured to provide desired properties. In some aspects, the island-of-the-sea microfibers may be sized from 1 micron to 5 microns and contain several nanofibers of the IR radiation transparent polymer held together by the sea component. The nanofibers are structured to be very fine fibers. The nanofibers within the island-in-the-sea microfiber may be sized from 50 nm to 1000 nm. In some aspects, the structure of the nanofibers may be affected by changing temperatures, voltage, application speeds, air speed, drawing ratio, and/or an extrusion die during the creation of the island-of-the-sea microfibers.

At operation 406, the island-of-the-sea microfibers are gathered and fabricated to form a fabric. The fabric may be woven, knitted, nonwoven and/or compound fabrics. The type of fabric created depends on the selected fabrication technique. In some aspects, the fabrication techniques are the same techniques utilized for conventional clothing materials.

Method 400 includes decision operation 408. At operation 408, a determination is made whether or not to dissolve the sea component. If the sea component is going to be dissolved, operation 410 is performed. If the sea component is not yet going to be dissolved, operation 412 is performed.

At operation 412, a garment is created from the microfiber fabric. The garment may be created from cutting, sewing, knitting, weaving, and/or any other suitable garment creating techniques. A garment may be clothing, outerwear, outdoor gear, and/or any other suitable application for IR radiation transparent fabric. More specifically, the garment may be a pair of pants, a shirt, a skirt, a jacket, a pair of shorts, a vest, a hat, a pair of gloves, a dress, a pair of leggings, a pair of capris, a bra, a piece of underwear, a piece of swim wear, a pair of shoes, etc. This list is exemplary only and is not meant to be limiting. Any item of clothing or outerwear that may be worn by a person or animal may be a garment as utilized herein.

Method 400 includes operation 410. Operation 410 is performed after operation 412 or after operation 408. At operation 410, the microfiber garment or microfiber fabric is washed with an appropriate solvent to dissolve the sea component from the microfibers utilizing hydrolysis. In some aspects, the sea component in the island-in-the-sea microfiber is polyvinyl alcohol. However, any suitable sea component may be utilized to create the island-in-the-sea microfibers. The solvent may be any suitable solvent for causing the sea component to dissolve utilizing hydrolysis.

The nanofibers created by dissolving the sea during operating 410 are aligned and run in the same direction. Further, the spaces formed between nanofibers may be controlled to create specifically sized micro pores that scatter visible light and are large enough to be air permeable. In some aspects, the micro pores are from 400 nm to 700 nm in diameter. In other aspects, the micro pores are from 800 nm to 1500 nm in diameter. As such, the nanofiber fabric or nanofiber garment created during operation 410 is IR radiation transparent and visibly opaque.

In some aspects, method 400 includes operation 414. At operation 414, a garment is created from the nanofiber fabric. The garment may be created from cutting, sewing, knitting, weaving, and/or any other suitable garment creating techniques.

Aspects of the present disclosure, for example, are described above with reference to block diagrams and/or operational illustrations of methods, systems, and computer program products according to aspects of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

This disclosure described some aspects of the present technology with reference to the accompanying drawings, in which only some of the possible aspects were described. Other aspects can, however, be embodied in many different forms and the specific aspects disclosed herein should not be construed as limited to the various aspects of the disclosure set forth herein. Rather, these exemplary aspects were provided so that this disclosure was thorough and complete and fully conveyed the scope of the other possible aspects to those skilled in the art. For example, aspects of the various aspects disclosed herein may be modified and/or combined without departing from the scope of this disclosure.

Although specific aspects were described herein, the scope of the technology is not limited to those specific aspects. One skilled in the art will recognize other aspects or improvements that are within the scope and spirit of the present technology. Therefore, the specific structure, acts, or media are disclosed only as illustrative aspects. The scope of the technology is defined by the following claims and any equivalents therein.

The description and illustration of one or more aspects provided in this application are not intended to limit or restrict the scope of the disclosure as claimed in any way. The embodiments, examples, and details provided in this application are considered sufficient to convey possession and enable others to make and use the best mode of claimed disclosure. The claims should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claims.

What is claimed is:

1. A method for creating an infrared radiation transparent and visible light opaque substrate, the method comprising:
   selecting an infrared radiation transparent and visible light transparent polymer;
   creating nanofibers out of the polymer, wherein micro pores are formed between the nanofibers,
   the micro pores scatter visible light to change the polymer from being visible light transparent to being visible light opaque;
   the micro pores are large enough to be air permeable, wherein the pores have a size from greater than 500 nm to 1500 nm; and
   forming an infrared radiation transparent and visible light opaque fabric from the nanofibers.

2. The method of claim 1, further comprising:
   creating a garment from the infrared radiation transparent and visible light opaque fabric,
   wherein the infrared radiation transparent and visible light opaque fabric is nonwoven.

3. The method of claim 1, further comprising:
   creating a garment from the infrared radiation transparent and visible light opaque fabric,
   wherein the infrared radiation transparent and visible light opaque fabric is woven.

4. The method of claim 1, wherein the polymer is polyethylene or polypropylene.

5. The method of claim 1, wherein creating nanofibers out of the polymer comprises electrospinning the polymer.

6. The method of claim 5, wherein the electrospinning is melt based or solution based.

7. The method of claim 1, wherein the polymer is a hydrocarbon, and
   wherein creating nanofibers out of the polymer comprises:
      applying island-in-the-sea extrusion to the polymer to form microfibers; and
      applying a solvent to the microfibers that dissolves a sea in the microfibers to form the nanofibers and the micro pores between the nanofibers.

8. The method of claim 1, wherein creating nanofibers out of the polymer comprises force spinning the polymer.

9. The method of claim 1, wherein creating nanofibers out of the polymer comprises hot air assisted melt electrospinning the polymer.

10. The method of claim 1, wherein creating nanofibers out of the polymer comprises melt blowing the polymer.

11. The method of claim 1, wherein the nanofibers have a diameter from 50 nm to 700 nm.

12. An infrared (IR) radiation transparent and visibly opaque substrate comprising:
   nanofibers of an IR radiation transparent polymer,
   wherein the nanofibers have a diameter from 50 nm to 1000 nm; and
   pores between the nanofibers large enough to scatter visible light and for air permeability,
   wherein the pores have a size from 400 nm to 1500 nm.

13. The substrate of claim 12, wherein the pores have a size from 400 nm to 700 nm in diameter.

14. The substrate of claim 12, wherein the pores have a size from 800 nm to 1500 nm in diameter.

15. The substrate of claim 12, wherein the substrate is a woven garment.

16. The substrate of claim 15, wherein the substrate is a garment,
   wherein the garment is one of one of: a pair of pants; a shirt; a skirt; a jacket; a pair of shorts; a vest; a hat; a pair of gloves; a dress; a pair of leggings; a pair of capris; a bra; a piece of underwear; a piece of swim wear; and a pair of shoes.

17. The substrate of claim 12, wherein the IR radiation transparent polymer is polypropylene.

18. The substrate of claim 12, wherein the IR radiation transparent polymer is polyethylene.

19. A method for creating an infrared radiation transparent and visible light opaque garment, the method comprising:
   selecting an infrared radiation transparent and visible light transparent polymer;
   creating island-of-the-sea microfibers from the polymer;
   creating a visible light transparent garment utilizing the microfibers; and
   applying a solvent to the garment that dissolves a sea component in the microfibers to form nanofibers of the polymer and to form pores between the nanofibers,
   wherein the pores are sized from 400 nm to 1500 nm and change the garment from visible light transparent to visible light opaque.

20. The method of claim 19, wherein creating the garment utilizing the microfibers comprises:
   weaving or knitting the microfibers to form a woven fabric; and
   at least one of sewing or cutting the woven fabric to form the garment.

* * * * *